United States Patent [19]

Levy et al.

[11] Patent Number: 5,746,775
[45] Date of Patent: May 5, 1998

[54] METHOD OF MAKING CALCIFICATION-RESISTANT BIOPROSTHETIC TISSUE

[75] Inventors: Robert J. Levy, Ann Arbor, Mich.; Danielle Hirsch, Jerusalem, Israel

[73] Assignee: The Board of Regent6s of the University of Michigan, Ann Arbor, Mich.

[21] Appl. No.: 140,722

[22] Filed: Oct. 21, 1993

Related U.S. Application Data

[63] Continuation-in-part of Ser. No. 689,652, Apr. 23, 1991, Pat. No. 5,368,608, which is a continuation-in-part of Ser. No. 515,484, Apr. 30, 1990, abandoned, which is a continuation-in-part of Ser. No. 176,789, Apr. 1, 1988, Pat. No. 5,094,661.

[51] Int. Cl.⁶ .................. A61F 2/02; A61F 2/24; D01C 3/00
[52] U.S. Cl. .................. 8/94.11; 8/94.28; 8/94.29; 623/1; 623/2; 623/3; 623/12; 623/66
[58] Field of Search .................. 8/94.11, 94.19, 8/94.28, 94.29; 623/1–3, 11, 12, 66

[56] References Cited

U.S. PATENT DOCUMENTS

| | | | |
|---|---|---|---|
| 713,046 | 11/1902 | Amend | 8/94.29 |
| 725,648 | 4/1903 | Amend | 8/94.29 |
| 2,750,251 | 6/1956 | Bloch et al. | 8/94.11 |
| 2,970,031 | 1/1961 | Nagy | 8/94.29 |
| 3,560,141 | 2/1971 | Kurilla et al. | 8/94.11 |
| 3,922,356 | 11/1975 | Cohly | 8/94.11 |
| 3,974,526 | 8/1976 | Dardik et al. | 3/1.4 |
| 4,097,234 | 6/1978 | Sohde et al. | 8/94.19 |
| 4,323,358 | 4/1982 | Lentz et al. | 8/94.11 |
| 4,378,224 | 3/1983 | Nimni et al. | 8/94.11 |
| 4,402,697 | 9/1983 | Pollack et al. | 8/94.11 |
| 4,405,327 | 9/1983 | Pollock | 8/94.11 |
| 4,481,009 | 11/1984 | Nashef | 8/94.11 |
| 4,553,974 | 11/1985 | Dewanjee | 8/94.11 |
| 4,597,960 | 7/1986 | Cohen | 424/435 |
| 4,647,283 | 3/1987 | Carpentier et al. | 623/11 |
| 4,648,881 | 3/1987 | Carpentier et al. | 623/11 |
| 4,729,139 | 3/1988 | Nashef | 8/94.11 |
| 4,753,652 | 6/1988 | Langer et al. | 8/94.11 |
| 4,770,665 | 9/1988 | Nashef | 8/94.11 |
| 4,786,287 | 11/1988 | Nashef et al. | 8/94.21 |
| 4,798,611 | 1/1989 | Freeman, Jr. | 8/94.11 |
| 4,838,888 | 6/1989 | Nashef | 623/2 |
| 4,885,005 | 12/1989 | Nashef et al. | 8/94.11 |
| 4,976,733 | 12/1990 | Girardot | 8/94.11 |
| 5,002,566 | 3/1991 | Carpentier et al. | 623/2 |
| 5,080,670 | 1/1992 | Imamura et al. | 623/2 |
| 5,215,541 | 6/1993 | Nashef et al. | 8/94.11 |
| 5,447,536 | 9/1995 | Girardot et al. | 8/94.11 |
| 5,476,516 | 12/1995 | Seifter et al. | 8/94.11 |

FOREIGN PATENT DOCUMENTS

| | | |
|---|---|---|
| A2-267434 | 5/1988 | European Pat. Off. . |
| WO 83/03335 | 10/1983 | WIPO . |
| WO 84/01879 | 5/1984 | WIPO . |
| WO 84/01894 | 5/1984 | WIPO . |

OTHER PUBLICATIONS

Okoshi, et al., A New Bioprosthetic Cardiac Valve With Reduced Calcification, *ASAIO Trans.* 1990, 36:M411–M414 (no month).

Tomizawa, et al., Development of a Polyepoxy Compound Cross–linked Heterologous Connective Tissue Tube, *ASAIO Journal* 1992, 38: M357–M361.

*Primary Examiner*—Walter D. Griffin
*Attorney, Agent, or Firm*—Rohm & Monsanto

[57] ABSTRACT

A method of treating a collagenous biomaterial, such as porcine aortic valve leaflets or bovine pericardium, by exposing the biomaterial to an alcohol to inhibit in vivo calcification. The biomaterial, preferably glutaraldehyde-pretreated, is subjected to an aqueous solution of 60% to 80% lower aliphatic alcohol, such as ethanol for a period of at least 20 minutes, and preferably, 24 to 72 hours. The biomaterial is rinsed, and then stored in either a glutaraldehyde-free environment or an ethanolic solution of glutaraldehyde. In some embodiments, the treatment solutions include an additional anticalcification agent which may be a soluble salt of a metallic cation, such as $Al^{+3}$ or $Fe^{+3}$.

32 Claims, 6 Drawing Sheets

METHOD OF MAKING CALCIFICATION-RESISTANT BIOPROSTHETIC TISSUE

RELATIONSHIP TO OTHER APPLICATIONS

This application is a continuation-in-part of U.S. patent application Ser. No. 07/689,652, filed on Apr. 23, 1991 now U.S. Pat. No. 5,368,608 issued on Nov. 29, 1994, as a continuation-in-part of Ser. No. 07/515,484 filed on Apr. 30, 1990, now abandoned, which in turn was a continuation-in-part of Ser. No. 07/176,789 filed on Apr. 1, 1988, now U.S. Pat. No. 5,094,661, issued on Mar. 10, 1992, all applications being assigned to the assignee hereof. The disclosure of the foregoing applications are incorporated herein by reference in their entirety.

GOVERNMENT RIGHTS CLAUSE

This invention was made with government support under Contract HL38118 awarded by the National Institutes of Health. The government has certain rights in the invention.

BACKGROUND OF THE INVENTION

This invention relates generally to materials which are resistant to in vivo calcification, and more particularly, to a method of preparing calcification-resistant biomaterials, such as bioprosthetic tissue, suitable for implantation in a living being.

More than 100,000 cardiac valve prostheses are placed in patients each year. Frequently, valve replacement surgery is the only means of treating cardiac valve disease. Currently used replacement valves include mechanical valves which may be composed entirely of a synthetic polymeric material such as polyurethane; bioprosthetic valves derived from bovine pericardium or porcine aortic valves; and aortic homografts.

Use of mechanical valves is frequently complicated by thrombosis and tissue overgrowth leading to valvular failure. Bioprosthetic heart valves have improved thrombogenicity and hemodynamic properties as compared to mechanical valve prostheses. However, calcification is the most frequent cause of the clinical failure of bioprosthetic heart valves fabricated from porcine aortic valves or bovine pericardium. Human aortic homograft implants have also been observed to undergo pathologic calcification involving both the valvular tissue as well as the adjacent aortic wall albeit at a slower rate than the bioprosthetic heart valves. Pathologic calcification leading to valvular failure, in such forms as stenosis and/or regurgitation, necessitates re-implantation. Therefore, the use of bioprosthetic heart valves and homografts has been limited because such tissue is subject to calcification. In fact, pediatric patients have been found to have an accelerated rate of calcification so that the use of bioprosthetic heart valves is contraindicated for this group.

Unfortunately, pathologic calcification also further complicates the use of synthetic vascular grafts and other artificial heart devices, such as ventricular assist systems, because it affects the flexibility of the synthetic polymers used to produce the devices.

The mechanism for pathological calcification of cardiovascular tissue is not fully understood. Generally, the term "pathologic calcification" refers to the undesirable deposition of calcium phosphate mineral salts. Calcification may be due to host factors, implant factors, and extraneous factors, such as mechanical stress. There is some evidence to suggest that deposits of calcium are related to devitalized cells, and in particular, cell membranes, where the calcium pump ($Ca^{+2}$—$Mg^{+2}$—ATPase) responsible for maintaining low intracellular calcium levels is no longer functioning or is malfunctioning. Calcification has been observed to begin with an accumulation of calcium and phosphorous, present as hydroxyapatite, which develops into nodules which can eventually lead to valvular failure.

The preparation of bioprosthetic tissue prior to implantation typically includes treatment to stabilize it against subsequent in vivo enzymatic degradation, typically by crosslinking molecules, particularly collagen, on and in the tissue. Various aldehydes have been used for this purpose, including glyoxal, formaldehyde, and glutaraldehyde. Glutaraldehyde, however, is the agent of choice. In addition to fixing the tissue, glutaraldehyde is a good sterilizing agent and it reduces the antigenicity of the tissue. To date, glutaraldehyde is the only effective crosslinking agent for preparing tissues for implantation that can be used at physiologic pH under aqueous conditions. Unfortunately, glutaraldehyde is now known to promote calcification. There is, thus, a need in the art for a means of reversing the calcification-promoting effects of crosslinking agents such as glutaraldehyde. It would be particularly desirable to incorporate anti-calcification agents into existing protocols for preparation of clinical-grade biomaterials.

Non-aldehyde crosslinking agents have been investigated, such as polyepoxides (e.g., polyglycerol polyglycidyl ethers sold under the trademark Denacol by Nagasi Chemicals, Osaka, Japan), but there have been no conclusive studies demonstrating efficacy of polyepoxide cross-linked tissues in vivo.

Research on the inhibition of calcification of bioprosthetic tissue has primarily focussed on tissue pretreatment with either detergents or diphosphonate anticalcification agents. Detergent pretreatment with noncovalently linked detergents, such as sodium dodecyl sulfate (SDS), and a covalently bound detergent, such as amino oleic acid, have been demonstrated to be efficacious to materials exposed in circulating blood. However, both detergents and diphosphonates tend to wash out of the implanted bioprosthetic tissue with time due to blood-material interactions. Thus, these treatments merely delay the onset of the inevitable calcification process. Accordingly, there is also a need for a means of providing long-term calcification resistance for bioprosthetic heart valves and other implantable biomaterials or devices which are subject to in vivo pathologic calcification.

In addition, detergents disadvantageously affect the tissue, resulting in a diminution of the collagen denaturation temperature, or shrink temperature ($T_s$), which is an important measure of material strength, durability, and integrity. In some cases, use of detergents results in local toxicity. There is, thus, a need for an effective method of imparting anti-calcification properties to bioprosthetic tissues which is not accompanied by the deleterious effects of detergents.

Further, all of the foregoing techniques still result in some degree of pathologic calcification in vivo as measured by calcium content of explanted specimens. There is, therefore, a need for a treatment that results in a greater level of calcification inhibition.

The use of alcohols in biomaterial treatment protocols is well-known, but is typically limited to its use as a solvent and/or sterilizing agent. For example, alcohol has been used in sterilizing rinses and for storage solutions. However, there has never been any teaching or suggestion that ethanol has any effect on prevention of pathologic calcification. It would be advantageous to use this well-known compound in existing protocols for rendering bioprosthetic tissue calcification-resistant.

It is, therefore, an object of this invention to provide a method of treating biomaterials, particularly glutaraldehyde-pretreated bioprosthetic tissue, to render the biomaterials resistant to in vivo pathologic calcification.

It is another object of this invention to provide a method of treating biomaterials to have a long-term, or prolonged, resistance to in vivo pathologic calcification.

It is also an object of this invention to provide a method of treating biomaterials to render the biomaterials resistant to in vivo pathologic calcification which can be easily incorporated into existing protocols for treatment of such materials, e.g., will permit the continued usage of the crosslinking agent glutaraldehyde.

It is a further object of this invention to provide a method of treating biomaterials to render the biomaterials resistant to in vivo pathologic calcification which has little, if any, deleterious effect on physical or mechanical properties of the tissue, such as shrink temperature ($T_s$).

It is a still further object of this invention to provide biomaterials suitable for implantation in a mammal which have improved resistance to in vivo pathologic calcification.

SUMMARY OF THE INVENTION

The foregoing and other objects are achieved by this invention which provides a method of treating a biomaterial, preferably glutaraldehyde-pretreated bioprosthetic tissue, such as porcine aortic valve components or bovine pericardium, with an alcohol to render the biomaterial resistant to calcification. The alcohol is preferably a lower aliphatic alcohol (C1 to C3), such as methanol, ethanol, propanol or isopropanol. In a preferred embodiment, the alcohol is ethanol.

The term "biomaterial" as used herein refers to collagenous material which may be derived from different animal, typically mammalian, species. The biomaterial is typically suitable for implantation, such as bioprosthetic tissue or the like, but the invention should not be limited thereby. Specific examples include, but are not limited to, heart valves, particularly porcine heart valves; aortic roots, walls, and/or leaflets; bovine pericardium; connective tissue derived materials such as dura mater; homograft tissues, such as aortic homografts and saphenous bypass grafts; tendons, ligaments, skin patches, arteries, veins; and the like. Of course, any other biologically-derived materials which are known, or become known, as being suitable for in-dwelling uses in the body of a living being are within the contemplation of the invention.

In accordance with a preferred embodiment of the invention, the biomaterial is pretreated with glutaraldehyde. Therefore, the alcohol treatment of the present invention can be incorporated into existing protocols and standard known methodologies for preparing bioprosthetic tissue for implantation. Of course, pretreatment of the biomaterial with other crosslinking agents is within the contemplation of the invention. In those embodiments wherein the biomaterial is crosslinked with glutaraldehyde, any of the variety of techniques for glutaraldehyde pretreatment may be used. In a typical glutaraldehyde pretreatment protocol, the biomaterial is exposed and/or stored in a solution of buffered glutaraldehyde under conditions suitable for crosslinking molecules on and in the biomaterial. For example, the biomaterial may be exposed to glutaraldehyde at appropriate temperatures (from about 4° C. to about 25° C.) and pH (from about 6 to about 8, preferably 7.1 to 7.4). Typical glutaraldehyde concentrations in the pretreatment solution range from about 0.2% to about 0.8% w/v or higher, and preferably 0.6%.

In accordance with the method of the invention, the amount of alcohol in the treatment solution is greater than about 50% by volume, and preferably in the range of 60% to 80%. The biomaterial is contacted with, or exposed to, the alcohol for a period of time sufficient to render the bioprosthetic tissue resistant to in vivo pathologic calcification, illustratively, from about 20 minutes (i.e., the period of time required for diffusion of ethanol, for example, into bioprosthetic tissue) to in excess of 96 hours. For some biomaterials, excessive exposure to the alcohol may result in a decrease in the anticalcification effects of the alcohol, or may necessitate rehydration of the tissue.

The length of time allotted for exposure in the embodiments described herein is illustrative and can be varied by those of skill in the art. For embodiments of the invention wherein the biomaterial is immersed, or soaked, in a liquid treatment solution of the alcohol, the exposure time is preferably between about 24 to 96 hours. However, longer exposure is within the contemplation of the invention provided appropriate storage conditions are maintained as will be described below. It should be noted, that no deleterious effects on the bioprosthetic tissue have been observed during the suggested period.

The manner in which the biomaterial is exposed to the alcohol includes, but is not limited to vapor, plasma, liquid, and/or cryogenic application of the alcohol. Irrespective of the method of exposure, the time period should be sufficient to promote alcoholic-collagen interactions which inhibit calcification, but not so long as to cause irreparable dehydration of the tissue by the alcohol.

In accordance with the method of the invention, the alcohol treatment solution is preferably liquid, and is water-based, i.e., is an aqueous solution of greater than about 50% alcohol, and preferably between 60% to 80% alcohol by volume, buffered to a pH between 6.0 and 8.0, and preferably between 7.0 and 7.6, and more preferably 7.4. Alternatively, a mixture of two or more organic solvents may be utilized in the practice of the invention provided that the combined volume of the organic solvents is greater than about 40%, preferably greater than about 50%. For example, a mixture of about 40% ethanol and about 40% acetone has proven effective (see, Example 7).

Suitable buffers for use in the practice of the invention are those buffers which have a buffering capacity sufficient to maintain a physiologically acceptable pH and do not cause any deleterious effects to the biomaterial or interfere with the treatment process. Exemplary buffers include, but are not limited to phosphate-buffered saline (PBS), and organic buffers, such as N-N-2-hydroxyethylpiperzine-N'-2-ethanesulfonic acid (HEPES) or morpholine propanesulphonic acid (MOPS); and buffers which include borate, bicarbonate, carbonate, cacodylate.

In preferred embodiments of the invention, the biomaterial is shaken, or agitated, during exposure to the alcohol treatment solution. Shaking can be accomplished in any manner, such as through use of an orbital shaker, or shaker stand. The alcohol treatment procedure is typically carried out at room temperature (25° C.). However, any temperature which is not deleterious to the tissue, for example 4° C. to about 37° C., is suitable for the practice of the invention.

While the discussion herein is directed to the concentration of alcohol in the treatment solution, e.g., 50% or greater, it is to be understood that alcohols, such as ethanol, diffuse rapidly into tissue so that the concentration of alcohol in solution is approximately the same as the regional concentration of alcohol in the tissue. Therefore, the definition of the term "exposure" is to be construed broadly enough to encompass the in situ release of alcohol in implanted tissue, such as that resulting from hydrolysis of tetraethyl esters, for example.

In preferred embodiments of the invention, the biomaterial, treated with alcohol as noted above to reduce calcification, should be rinsed prior to implantation or storage to remove excess alcohol and other deleterious components produced or used in the biomaterial treatment protocol, such as aldehyde fragments from the glutaraldehyde pretreatment. As used herein, the term "rinse" includes subjecting the biomaterial to a rinsing solution, including continuously or by batch processing, wherein the biomaterial is placed in a rinsing solution which may be periodically removed and replaced with fresh solution at predetermined intervals. During rinsing, the tissue is preferably shaken, or intermittently stirred, to ensure even distribution of the rinse solution. Rinsing may be accomplished by subjecting the biomaterial to a rinsing solution, such as fresh HEPES buffer at pH 7.4. Illustratively, a rinse may comprise soaking the biomaterial in fresh rinsing solution which is replaced three times over a period of about 5 to 15 minutes. Alternatively, the rinsing solution may be replaced at intervals of 6 to 8 hours, or less, over a rinse period of 24 hours. In a preferred embodiment, the HEPES buffer is replaced each hour over a rinse period of 24 hours. As used herein, the longer rinse periods are referred to as "washes."

Exemplary rinsing solutions include physiologically suitable solutions, such as water, saline, PBS, HEPES buffered saline, ringers lactate (pH 7.4), sodium bicarbonate (pH 7.4), tris (pH 7.4), and imidazole (pH 7.4).

Subsequent to rinsing, the treated bioprosthetic tissue is ready for implantation or may be sterilized and stored until use. Storage in standard glutaraldehyde solutions of the type typically used for long-term storage of clinical-grade bioprostheses may partially reverse the beneficial effects achieved by the alcohol treatment of the present invention (see, FIG. 2). In accordance with some embodiments of the invention, the treated biomaterial may be stored in an ethanolic-glutaraldehyde solution, preferably in an amount sufficient to maintain calcification inhibition and/or sterility. In a preferred embodiment, the treated biomaterial is stored in a buffered alcohol solution containing glutaraldehyde, typically greater than about 60%, and preferably between about 60% and about 80%, alcohol and less than about 0.5%, preferably between about 0.2% to 0.5%, glutaraldehyde. In a particularly preferred embodiment, the storage solution is 60% ethanol and 0.2% glutaraldehyde (see Table 6 below).

In other embodiments of the invention, biomaterials which have been treated in accordance with the method of the invention are stored in an aldehyde-free environment. In preferred embodiments, treated bioprostheses are placed in sterile bags and subjected to sterilizing radiation, such as gamma-radiation. Of course, the ethanol treatment of the present invention is compatible with many other known sterilizing preservatives and/or techniques which are known, or can be developed, by those of skill in the art.

In accordance with a further method embodiment of the invention, the alcohol treatment solution may also contains one or more additional anticalcification agents, including but not limited to, a soluble salt of a metallic cation, such as Al$^{+3}$ or Fe$^{+3}$, preferably in a concentration range of 0.1M to 0.001M. Water soluble aluminum salts, for example, which are suitable additional anticalcification agents for use in the practice of the present invention, include without limitation, aluminum chlorate, aluminum lactate, aluminum potassium sulfate, aluminum sodium sulfate, aluminum sulfate, aluminum nitrate, and aluminum chloride. In a preferred embodiment, the soluble salt is AlCl$_3$ at 0.1M concentration. Also, water-soluble ferric salts, such as ferric chloride, ferric nitrate, ferric bromide, ferric sodium edentate, ferric sulfate, and ferric formate, are specifically included within the contemplation of the invention. Of course, any salt of aluminum, or iron, which is soluble in the solvent system of the treatment solution, may be used in the practice of the invention.

Other embodiments of the invention include the biomaterials which have been produced by a method according to the invention. In preferred embodiments of the invention, these biomaterials exhibit improved anti-calcification properties, and/or long-term resistance to in vivo pathologic calcification.

BRIEF DESCRIPTION OF THE DRAWINGS

Comprehension of the invention is facilitated by reading the following detailed description, in conjunction with the annexed drawings, in which.

DETAILED DESCRIPTION

Given below are several specific illustrative techniques for producing calcification-resistant biomaterials in accordance with the principles of the invention. Although the examples given are primarily directed to the preparation of calcification-resistant heart valves, the techniques described herein are applicable to the creation of any other biomaterials, particularly a prosthesis or a bioprosthetic tissue suitable for implantation.

Further, although the results have been presented in the form of rat subdermal implants and sheep bioprosthetic heart valve replacement studies, it should be noted that these animal model systems result in calcific deposits which closely resemble those seen in clinical-pathological explant of human tissue. The correspondence of these animal models with human pathology has been documented in both light microscopic and electron microscopic studies.

Glutaraldehyde-pretreated porcine aortic heart valves, both in stent and freestyle (stentless) form, were obtained from St. Jude Medical, Inc., St. Paul, Minn. and from Medtronic, Inc., Irvine, Calif. and used in the examples set forth below. Typically, the biomaterials are stabilized and preserved in glutaraldehyde following harvesting, illustratively in a 0.5% solution of glutaraldehyde in a buffer.

EXPERIMENTAL SECTION

Example 1

Figure 1:
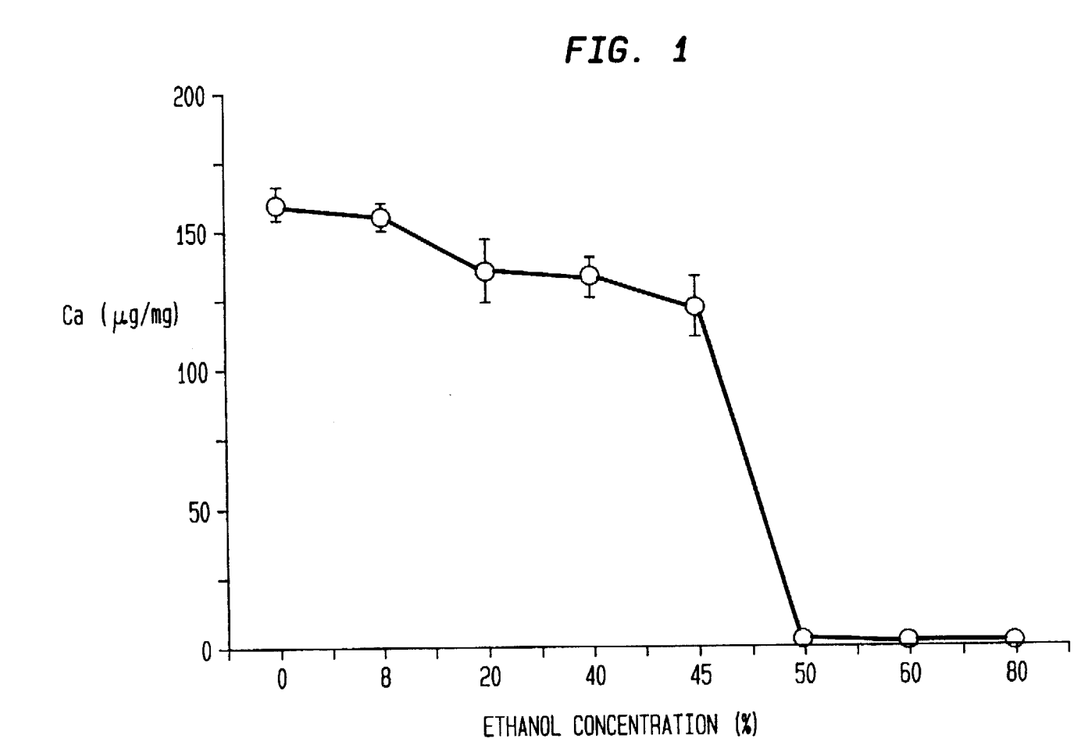
FIG. 1 is a graphical representation of the inhibition of porcine aortic valve calcification in a rat subdermal model for porcine aortic valve specimens (cusps) treated in accordance with a method of the invention.

A dose response study was conducted and the results are shown graphically in FIG. 1. Glutaraldehyde-pretreated porcine aortic valve specimens were immersed for 24 hours in aqueous solutions of ethanol ranging in concentration from 0% (control) to 80% ethanol. The ethanol solutions were buffered at pH 7.4 with HEPES (0.05M). The treated porcine aortic valve specimens were implanted in two subcutaneous pouches dissected in the ventral abdominal wall of weanling rats (male, CD, Sprague-Dawley, weighing 50–60 gm). After a period of 21 days, the specimens were removed and examined for calcification by measuring the level of $Ca^{+2}$ ions in the specimen. Concentrations of 50% or greater of ethanol virtually eliminated calcium accumulation in the porcine aortic valve specimens as compared to glutaraldehyde-pretreated controls.

Example 2

Figure 2:
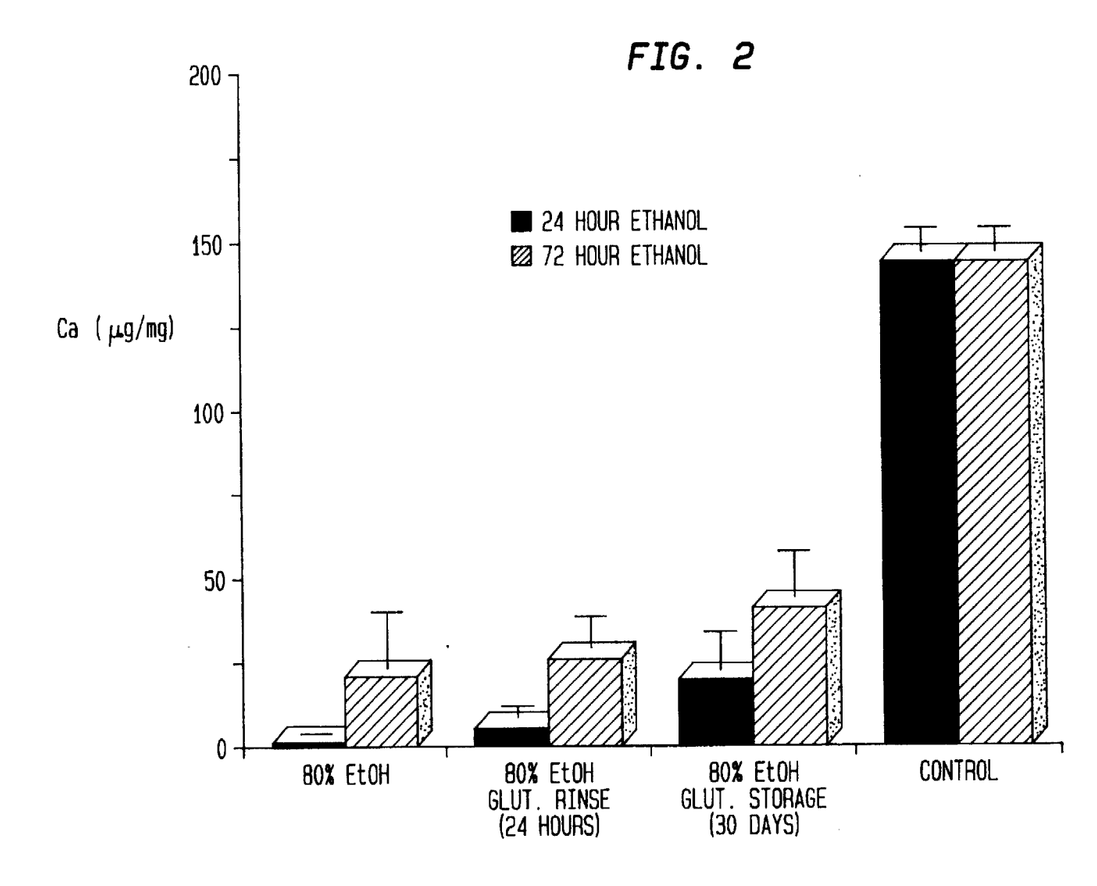
FIG. 2 is a graphical representation of the calcium content (µg/mg) of porcine aortic valve specimens, treated in accordance with a method of the invention, following 21 day subdermal implantation in rats.

Studies were conducted on porcine aortic valve specimens to determine the length of time of exposure to the alcohol treatment solution which is required for optimal anticalcification effects. FIG. 2 is a graphical representation of the calcium content (µg/mg) of glutaraldehyde-pretreated porcine aortic valve cusp specimens, following 21 day implantation in rat subdermal pouches, which have been exposed to 80% ethanol for periods of 24 hours and 72 hours. Typically, 72 hours of exposure to ethanol results in more calcium accumulation than 24 hours of exposure. However, calcification levels following 72 hours exposure to ethanol were nevertheless consistently below the level of controls (glutaraldehyde-pretreated porcine aortic valve cusps). The calcium content of the control specimens was 178.2±6.166 µg/mg dry tissue whereas the calcium content of the specimens which were subjected to 24 hours exposure to 80% ethanol, followed by a rinse with three 100 ml portions of HEPES buffered saline (pH 7.4) over about a 10 to 15 minute period, was 2.248±0.186 µg/mg. This represents 99% inhibition, i.e., substantial inhibition.

Referring again to FIG. 2, the calcium content of ethanol treated porcine aortic valve specimens, subsequently rinsed or stored in a glutaraldehyde-containing solution, is shown. In one instance ("Glut. Rinse"), the ethanol treated specimens were rinsed in three 100 ml portions of 0.2% glutaraldehyde buffered to a pH of 7.4 (HEPES) over about a 15 minute rinse period. In the second instance ("Glut. Storage"), the ethanol treated specimens were stored in 0.2% glutaraldehyde buffered to a pH of 7.4 (HEPES) for 30 days, and then rinsed with HEPES buffered saline prior to implant. Contact with, or storage in, a glutaraldehyde-containing solution resulted in more calcium accumulation than observed in those specimens maintained free of additional exposure to glutaraldehyde.

Example 3

Rinsing, or washing, was found to produce significant effects on the level of calcification in 21 day and 60 day rat subdermal implant studies as reported below in Table 1. Table 1 presents the calcium content of a set of porcine aortic heart valve specimens following implantation in a rat subdermal pouch. The specimens were untreated glutaraldehyde-pretreated porcine aortic heart valves obtained from St. Jude Medical, Inc. (control) and treated glutaraldehyde-pretreated porcine aortic heart valves which had been subjected to 80% ethanol for 24 hours. The 80% ethanol treated specimens were then subjected to a last minute "wash" (24 hour immersion in pH 7.4 HEPES buffered saline, changed hourly), or "rinse," (defined as three one minute, 100 ml rinses with pH 7.4 HEPES buffered saline). Additional 80% ethanol treated specimens were stored in a solution of 80% ethanol and 0.2% glutaraldehyde buffered to a pH of 7.4 (HEPES) for 1 month and then subjected to a "rinse" or "wash."

TABLE 1

| Treatment Group | 21 day $Ca^{+2}$ (µg/mg) | 60 day $Ca^{+2}$ (82 g/mg) |
|---|---|---|
| Control | 183.15 ± 0.03 | 236.3 ± 6.14 |
| 80% ethanol/rinse | 11.1 ± 6.04 | 14.6 ± 10.5 |
| 80% ethanol/wash | 5.16 ± 1.72 | 1.87 ± 0.29 |
| 80% ethanol/Glut. storage/rinse | 3.13 ± 1.67 | 22.9 ± 8.14 |
| 80% ethanol/Glut. storage/wash | 4.11 ± 2.4 | 18.3 ± 8.31 |

Specimens of glutaraldehyde-pretreated bovine pericardium were treated in 80% ethanol followed by a 24 hour wash. The calcium content of rat subdermal implants following 21 days was 2.95±0.78 µg/mg. In comparison, the calcium content of untreated control specimens was 121.16±7.49 µg/mg.

Example 4

Figure 3:
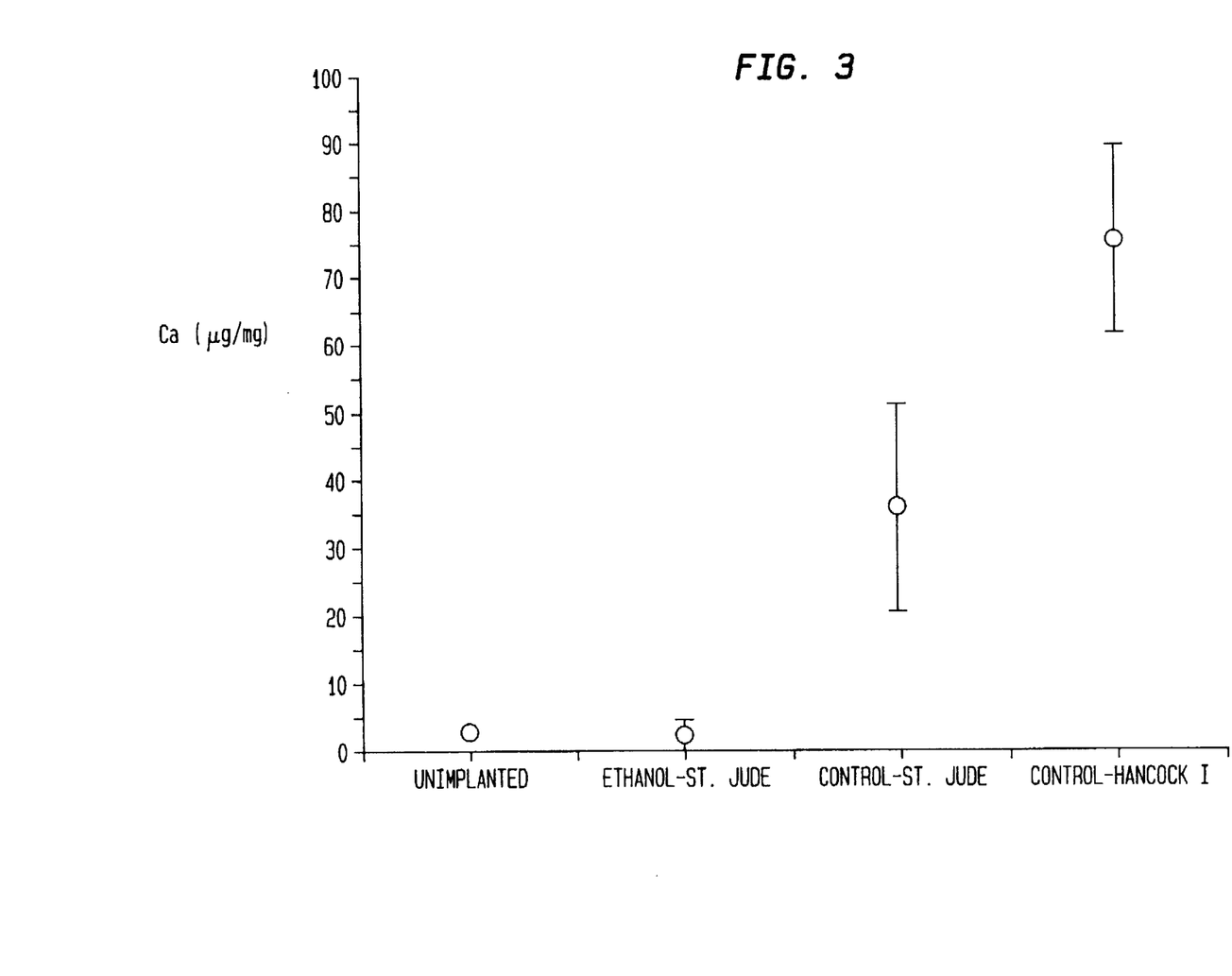
FIG. 3 is a graphical representation of the calcium content (µg/mg) of various porcine aortic valve specimens implanted in sheep for 150 days.

Studies were conducted with glutaraldehyde-pretreated porcine aortic heart valve specimens in order to assess efficacy of the method of the present invention for calcification-resistance in vivo. Glutaraldehyde-pretreated porcine heart valve specimens were obtained from St. Jude Medical, Inc. (St. Jude) and from Medtronic, Inc., (Hancock I). Control specimens were not exposed to alcohol treatment. Experimental specimens were subjected to 80% ethanol for 72 to 96 hours. Control and experimental specimens were implanted in juvenile sheep as mitral valve replacements. Five months after implant, the valves were explanted and analyzed for calcium content. The results are shown in FIG. 3 which is a graphical representation of the calcium content (µg/mg) of the explanted specimens (10 sheep per group) at 150 days. Complete inhibition of calcification is shown by ethanol treatment. For comparative purposes, the calcium content of fresh, unimplanted porcine aortic heart valve specimens is shown.

Example 5

While not wishing to be bound by a particular theory, it is postulated that the alcohol irreversibly alters the devitalized membrane of glutaraldehyde-pretreated bioprosthetic tissues. Proton NMR studies show an altered association with water following alcohol treatment. Table 2 shows the T1 and T2 relaxation times for proton NMR measurements (7.5 Tesla instrument) conducted on fresh porcine aortic heart valve specimens, as well as glutaraldehyde-pretreated specimens and glutaraldehyde-pretreated specimens which have been subjected to treatment in 80% ethanol in accordance with the principles of the invention. Treatment with ethanol results in significantly prolonged T1 and T2 relaxation times indicating a water-rich environment which is much less conducive to calcium phosphate precipitation.

TABLE 2

| | T1 (sec) | T2 (msec) |
|---|---|---|
| Untreated | 1.84 ± 0.19 | 0.14 ± 0.1 |
| Glutaraldehyde | 1.78 ± 0.31 | 0.30 ± 0.05 |
| Ethanol | 2.36 ± 0.36 | 0.42 ± 0.027 |

*Porcine aortic heart valve leaflets: as retrieved with no treatment (UNTREATED); treated with 0.6% glutaraldehyde (GLUTARALDEHYDE; treated with 80% ehtanol (ETHANOL.) All treatment solutions were buffered to pH 7.4.

Example 6

Figure 4:
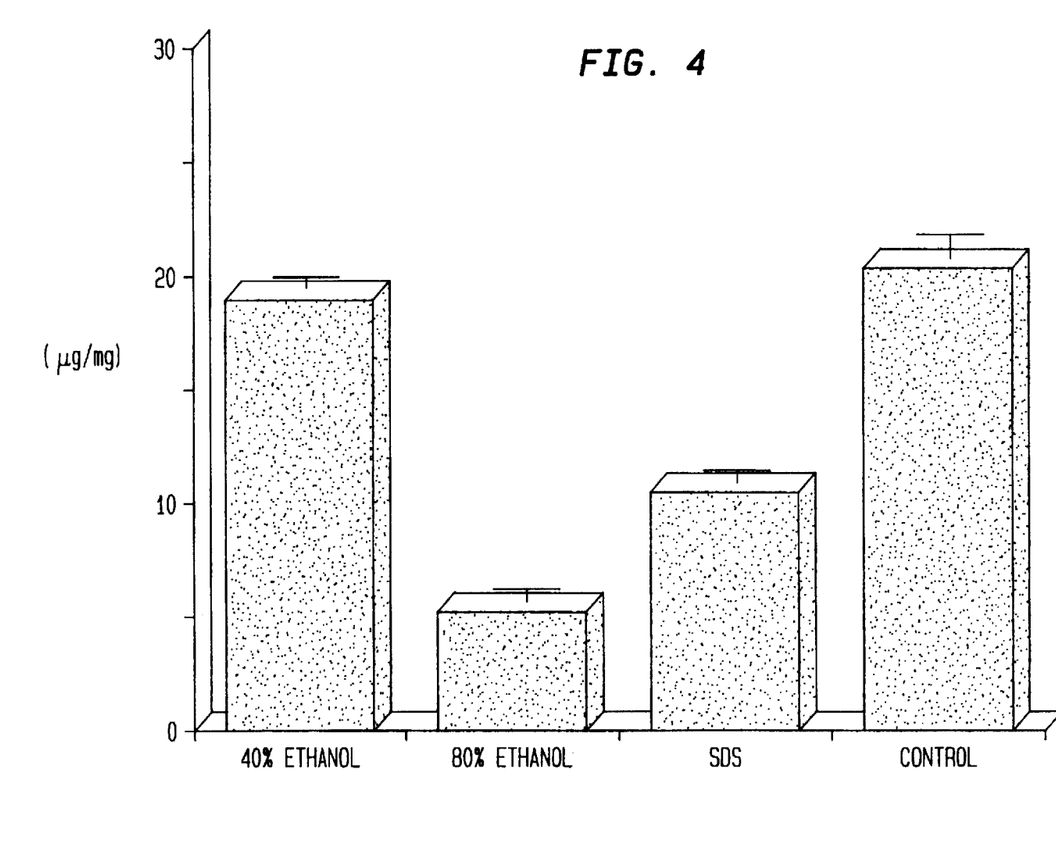
FIG. 4 is a graphical representation of the $^{14}$C cholesterol content, in µg/mg, of glutaraldehyde-pretreated porcine aortic valves as compared to glutaraldehyde-pretreated porcine aortic valves which have been treated with an aqueous solution of ethanol (40% and 80%) in accordance with a method of the invention, or with detergent (1% sodium dodecyl sulfate, SDS)

Alcohol treatment almost completely removes all cholesterol and phospholipids from the tissue and appears to block the uptake of plasma lipoproteins into the biomaterial. Specimens of glutaraldehyde-pretreated porcine aortic valves (cusps) were subjected to treatment in 40% ethanol, 80% ethanol, and detergent (1% SDS) for 24 hours. Untreated, glutaraldehyde-pretreated porcine aortic valve specimens were used as the control. The specimens were placed in a solution of $^{14}$C-cholesterol in bovine serum for 24 hours. FIG. 4 is a graphical representation of the cholesterol content, in µg/mg, of the treated specimens and the control. Cholesterol uptake by porcine aortic valve specimens was found to be diminished in specimens subjected to 80% ethanol for 24 hours, possibly indicating a permanent material effect which blocks the uptake of plasma lipoproteins. Detergent-treated tissue exhibited significantly higher cholesterol uptake.

Table 3 presents the total cholesterol (CS) and phospholipid (PL) content of glutaraldehyde-pretreated porcine aortic valve specimens treated for 24 hours in either buffered aqueous solutions of alcohol or chloroform-methanol as identified therein.

TABLE 3

| GROUP | Total CS* (nmole/mg) | PL* (nmole/mg) |
|---|---|---|
| Control (glu.) | 13.34 ± 0.41 | 17.24 ± 0.85 |
| 40% Ethanol | 13.96 ± 0.71 | 16.5 ± 1.49 |
| 60% Ethanol | 0.30 ± 0.05 | 4.93 ± 1.91 |
| 80% Ethanol | 0.14 ± 0.02 | 1.08 ± 0.11 |
| 1% SDS | 1.40 ± 0.1 | 0.94 ± 0.05 |
| 2:1 CHCl$_3$:Methanol | 0.10 ± 0.0 | 0.57 ± 0.07 |
| 80% Methanol | 0.28 ± 0.02 | 2.62 ± 0.36 |
| 80% Acetone | 0.12 ± 0.02 | 1.94 ± 0.32 |
| 80% Acetonitrile | 0.16 ± 0.04 | 2.76 ± 0.28 |

*Mean ± SEM (N = 5)

As shown in Table 3, 80% ethanol exposure removes virtually all of the cholesterol and phospholipids contained in the porcine aortic valve tissue. Detergent (SDS) had a significantly diminished effect on tissue cholesterol and phospholipid content as compared to 60% or greater ethanol.

Example 7

Figure 5:
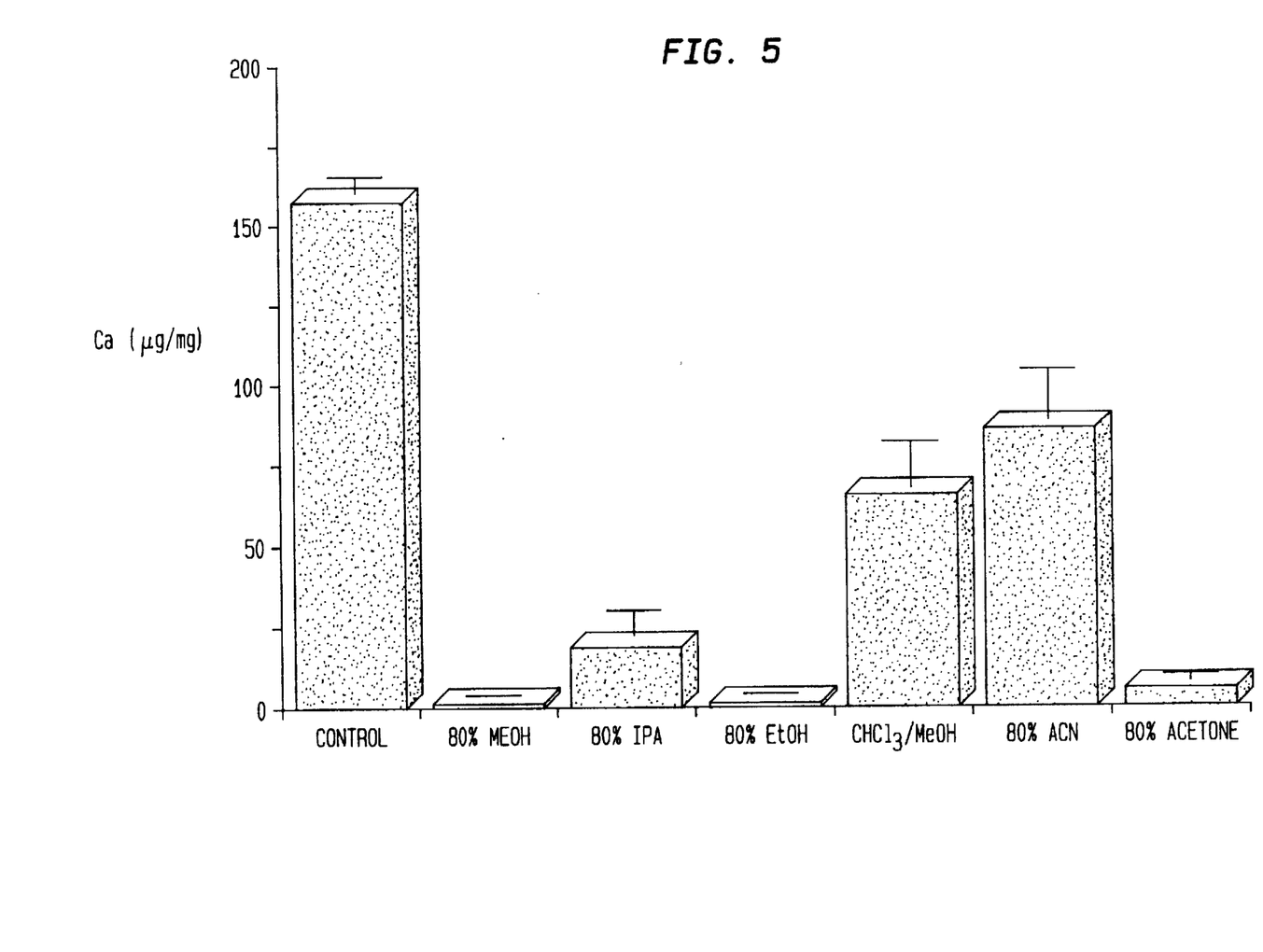
FIG. 5 is a graphical representation of the calcification content of glutaraldehyde-pretreated porcine aortic valve specimens which have been subjected to a variety of solvents known to remove lipids from tissues.

Other solvents which are also known to extract cholesterol and lipids were investigated for possible anticalcification effects. Specimens of glutaraldehyde-pretreated porcine aortic valve cusps (control) were subjected to: 80% methanol, 80% isopropanol, 80% ethanol, chloroform/methanol (2:1), 80% acetonitrile, and 80% acetone for 24 hours. The specimens were implanted in subdermal pouches in rats for 21 days and the calcium content was ascertained at explant. The results are shown graphically on FIG. 5. While methanol and acetone exhibited comparable antical-cification effects to that of ethanol, the use of these solvents is problematic inasmuch as residual methanol is potentially toxic in an implantation environment and acetone may be carcinogenic. Surprisingly, chloroform/methanol, which is the standard solution for extracting lipids, was significantly less effective than ethanol.

In another related study, a combined concentration effect was observed with 40% ethanol and 40% acetone. Individually, neither of these solvents are effective at 40% concentration (see, FIG. 1 for ethanol efficacy at 40% concentration). The calcium content of implanted porcine aortic heart valve specimens which were subjected to 40% acetone, after 21 days in a rat subdermal pouch, was 141.07±28.91 µg/mg. Whereas, the calcium content of specimens subjected to a mixture of 40% ethanol and 40% acetone was 1.54±0.16 µg/mg. Thus, a mixture of two or more solvents may be utilized in the practice of the invention provided that the combined volume of the organic solvents is greater than 50%.

Example 8

Figure 6:
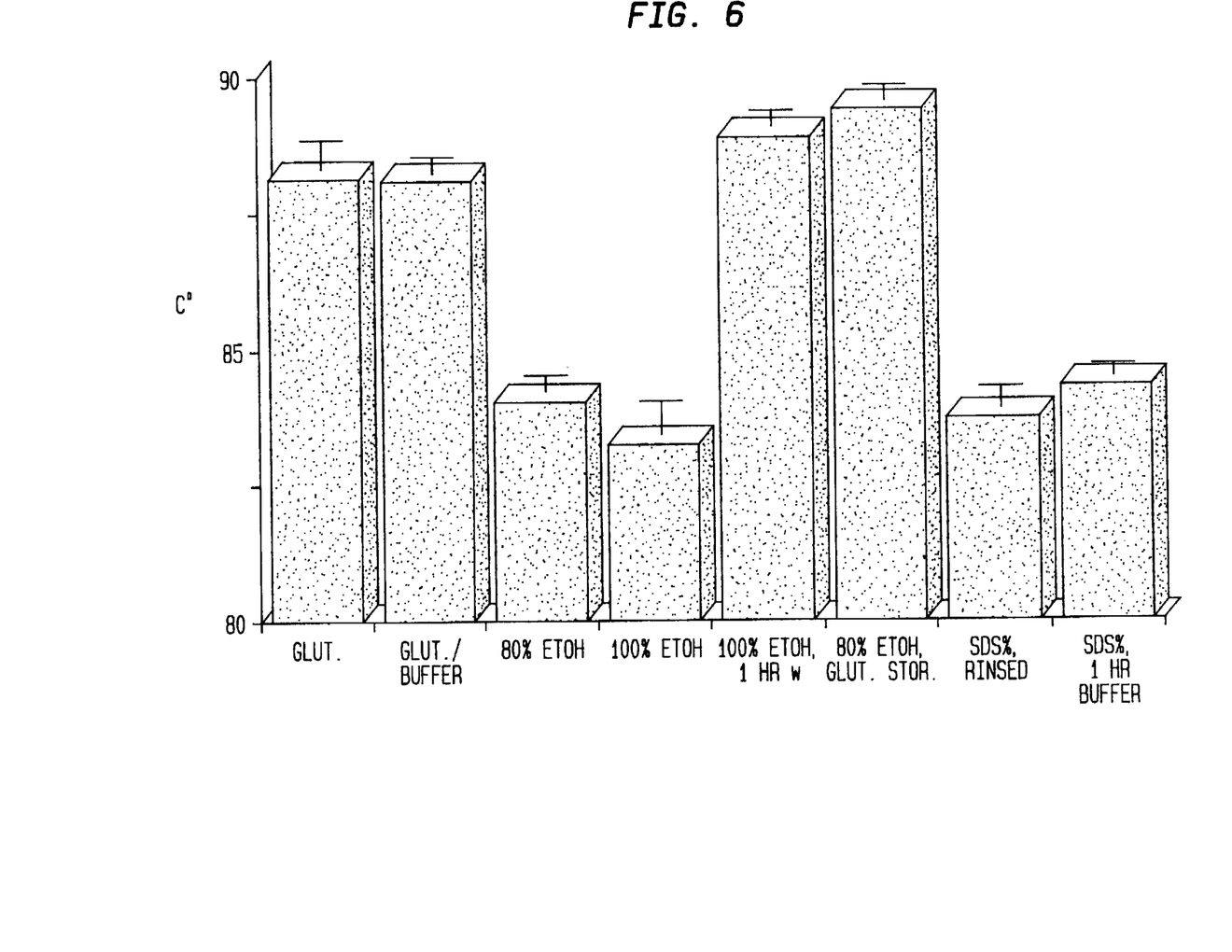
FIG. 6 is a graphical representation of $T_s$ in °C. for porcine aortic valve specimens subjected to various ethanol treatment and storage regimens.

$T_s$, which is an important measure of material strength, durability, and integrity, is almost completely unaffected by the ethanol treatment of the present invention as shown in FIG. 6. FIG. 6 is a graphical representation of the collagen denaturation temperature (°C.) for specimens of glutaraldehyde-pretreated porcine aortic valves (cusps) subjected to various treatment schemes, specifically 24 hours of exposure to ethanol (80% or 100%) and detergent (SDS). The schemes include: 80% ethanol without rinsing; 100% ethanol without rinsing; 100% ethanol followed by washing with HEPES buffered saline for 1 hour; 80% ethanol followed by rinsing with HEPES buffered saline and storage in 0.2% glutaraldehyde for 24 hours; 1% SDS followed by a HEPES buffered saline rinse; and 1% SDS followed by washing with HEPES buffered saline for 1 hour. The controls were glutaraldehyde-pretreated porcine aortic valve specimens obtained from St. Jude Medical, Inc., either as received ("Glut."), or as rinsed and stored in pH 7.4 HEPES buffered saline for 24 hours ("Glut./Buffer"). Differential scanning calorimetry was used to obtain the data. Ethanol treatment, followed by aqueous rinsing and appropriate storage conditions, had no effect on $T_s$, whereas detergent treatment significantly lowered $T_s$.

Differential scanning calorimetry was used to ascertain the amount of time required to rehydrate porcine aortic valve specimens after exposure to 80% ethanol for 24 hours. As used herein, the term "rehydrate" refers to restoring $T_s$ to the value of control (glutaraldehyde-pretreated porcine aortic valve specimens which were rinsed in pH 7.4 HEPES buffered saline for 24 hours). The ethanol treated specimens (cusps) were subjected to HEPES buffered saline (pH 7.4) for varying time periods, ranging from a rinse (i.e., pouring rinse solution over the specimen) to one hour. The results are shown in Table 4. A two minute rinse returns $T_s$ of the treated specimens to a value which is not significantly different, statistically, from the $T_s$ value of the control.

TABLE 4

| Treatment | Rinse Period | $T_s$ (°C.) |
|---|---|---|
| Control | 24 hrs | 88.33 ± 0.56 |
| 80% EtOH | rinse | 84.06 ± 0.32 |
| 80% EtOH | 1 min. | 84.49 ± 0.39 |
| 80% EtOH | 2 min. | 87.41 ± 0.23 |

TABLE 4-continued

| Treatment | Rinse Period | $T_s$ (°C.) |
|---|---|---|
| 80% EtOH | 5 min. | 87.85 |
| 80% EtOH | 10 min. | 87.54 |
| 80% EtOH | 1 hr | 87.38 ± 0.26 |

Example 9

The overall protein composition and valvular morphology of porcine aortic valves are unaffected by alcoholic treatment as demonstrated by complete amino acid analysis and electron spectroscopy for chemical analyses (ESCA). In fact, alcohol treatment enhances surface smoothing and anisotrophy of porcine aortic valve leaflets resulting in a surface chemistry which is comparable to fresh leaflets. In contrast, glutaraldehyde-pretreated (control) or detergent (SDS) treated tissue show significant differences. Table 5 hereinbelow presents ESCA data of the surface carbon (C1s), nitrogen (N1s), and oxygen (O1s) concentrations (%) in porcine aortic valve specimens immersed for 24 hours in the indicated solution.

TABLE 5

| GROUP | ATOMIC CONCENTRATION (%) | | |
|---|---|---|---|
| | O1s | N1S | C1s |
| Fresh Tissue | 20.41 | 10.06 | 69.52 |
| 80% Ethanol | 21.89 | 11.93 | 66.18 |
| 40% Ethanol | 16.45 | 7.78 | 75.76 |
| Glutaraldehyde-Fixed | 14.46 | 7.22 | 78.32 |
| 1% SDS | 19.03 | 7.37 | 73.6 |
| 2:1 CHCl$_3$/MeOH | 22.71 | 15.85 | 61.44 |

Complete amino acid analyses of ethanol treated, glutaraldehyde-pretreated porcine aortic valves as compared to glutaraldehyde-pretreated porcine aortic valves revealed that ethanol treatment has virtually no effect on the amino acid compositions, i.e., ethanol treatment does not extract to any significant extent any of the protein components of bioprosthetic tissue.

Functional in vitro testing for mechanical and physiologic valve function demonstrated that mechanical functioning is improved by ethanol treatment in accordance with the present invention.

Example 10

In a series of experiments to exemplify additional embodiments of the invention, specimens of glutaraldehyde-pretreated porcine aortic valves were treated with 60% ethanol in a variety of protocols. Although the term "porcine aortic valves" generally includes both the valve cusps, or leaflets, and an aortic wall portion, the prior experiments reported hereinabove were conducted primarily on valve cusp tissue. In the present experiments, the two types of tissue have been separated and the data reported separately on Table 6.

Glutaraldehyde-pretreated bioprosthetic heart valve specimens, obtained from St. Jude Medical, Inc., were used as controls. Specimens of the glutaraldehyde-pretreated tissue were then subjected to treating solutions of 60% ethanol, or 60% ethanol and 0.1M AlCl$_3$, for 24 hours. Following ethanol treatment, the tissue was rinsed for 24 hours in neutral buffer, specifically HEPES at pH 7.4. Subsequent to rinsing, the tissue samples were sterilized and stored for 14 days. In some storage protocols, the tissue was packaged in neutral buffer and subjected to sterilizing radiation. In other storage protocols, the tissue was stored in solutions of 60% ethanol and glutaraldehyde (0.2% or 0.5%). In yet further storage protocols, the storage solution additionally contained 0.1M AlCl$_3$.

The tissue samples prepared as described above were implanted in rat subdermal pouches and analyzed for calcium content after 21 days. The results are reported below in Table 6.

TABLE 6

| Exp. No. | Treatment | Storage Rinse (14 Days) | µg Ca/Mg Cusp | Wall |
|---|---|---|---|---|
| 1 | 24 hr 60% EtOH | 24 hr Buffer + Irrad. | 13.763 ± 3.550 | 40.892 ± 6.057 |
| 2 | 24 hr 60% EtOH + 0.1 M AlCl$_3$ | 24 hr Buffer + Irrad. | 6.836 ± 0.262 | 2.75 ± 0.745 |
| 3 | 24 hr 60% EtOH | 24 hr 60% EtOH + 0.2% Glut. | 9.157 ± 3.733 | 50.470 ± 1.628 |
| 4 | 24 hr 60% EtOH + 0.1 M AlCl$_3$ | 24 hr 60% EtOH + 0.2% Glut. | 7.029 ± 0.592 | 7.110 ± 0.915 |
| 5 | 24 hr 60% EtOH | 24 hr 60% EtOH + 0.5% Glut. | 8.791 ± 2.716 | 49.082 ± 4.217 |
| 6 | 24 hr 60% EtOH + 0.1 M AlCl$_3$ | 24 hr 60% EtOH + 0.5% Glut. | 8.689 ± 0.367 | 8.449 ± 0.341 |
| 7 | none | none 60% EtOH + | 1.952 ± 0.446 | 60.690 ± 4.716 |
| 8 | none | none 60% EtOH + 0.2% Glut. + 0.1 M AlCl$_3$ | 10.326 ± 0.635 | 12.782 ± 3.469 |
| 9 | none | none 60% EtOH + 0.5% Glut. | 7.907 ± 3.635 | 39.810 ± 5.026 |
| 10 | none | none 60% EtOH + 0.5% Glut. + 0.1 M AlCl$_3$ | 9.568 ± 0.240 | 7.763 ± 0.368 |

TABLE 6-continued

| Exp. No. | Storage Treatment | Rinse (14 Days) | μg Ca/Mg Cusp | Wall |
|---|---|---|---|---|
| Control (No Treatment) | — | — | 107.059 ± 3.239 | 49.915 ± 2.160 |

As shown in Table 6, in embodiments where the biomaterial is specifically aortic wall tissue, incorporation of $Al^{+3}$ in the treatment solution, or storage solution, results in much greater inhibition of calcification than treatment with an alcohol solution.

Example 11

Specimens of the glutaraldehyde-pretreated porcine aortic wall tissue were subjected, for 24 hours, to aqueous (pH 7.4 buffered HEPES) treating solutions of 0.1M $FeCl_3$; 0.01M $FeCl_3$; 80% ethanol; 80% ethanol and 0.1M $FeCl_3$; and 80% ethanol and 0.01M $FeCl_3$. Following treatment, the tissue was rinsed in three 100 ml portions of neutral buffer, specifically HEPES at pH 7.4. Specimens of glutaraldehyde-pretreated porcine aortic wall tissue, obtained from St. Jude Medical, Inc., were used as controls. The tissue samples, prepared as described above, were implanted in rat subdermal pouches and analyzed for calcium content after 21 days. The results are reported below in Table 7.

TABLE 7

| TISSUE | PRETREATMENT | WASHING | Ca (μg/mg) |
|---|---|---|---|
| Porcine Aortic Wall | Control | No | 36.46 ± 4.04 |
| | 0.1 M $FeCl_3$ | Rinse | 13.37 ± 1.5 |
| | 0.01 M $FeCl_3$ | Rinse | 13.52 ± 2.93 |
| | 80% EtOH | Rinse | 18.55 ± 3.61 |
| | 80% EtOH + 0.1 M Fe | Rinse | 6.31 ± 0.55 |
| | 80% EtOH + 0.01 M Fe | Rinse | 7.01 ± 1.03 |

Table 7 demonstrates that incorporation of $Fe^{+3}$ ions in the alcohol treatment and/or storage solutions will produce improved resistance to calcification for porcine aortic wall specimens.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:

1. A method of treating a biomaterial, the method comprising the steps of:

(1) forming a liquid treatment solution consisting essentially of greater than 50% by volume of a water-soluble C1–C3 aliphatic alcohol in an aqueous buffer of a pH between 6.0 and 8.0;

(2) exposing the biomaterial, wherein the biomaterial is a collagenous material derived from a mammalian species selected from the group consisting of bovine pericardium, porcine aortic heart valves, saphenous bypass grafts, aortic homografts, and dura mater, to the liquid treatment solution for a period of time sufficient to render the biomaterial resistant to calcification; and (3) rinsing the exposed biomaterial with a rinsing solution.

2. The method of claim 1 wherein the biomaterial rendered resistant to calcification is rendered resistant to in vivo pathologic calcification.

3. The method of claim 1 wherein said step of exposing comprises immersing the biomaterial in the liquid treatment solution.

4. The method of claim 3 wherein the alcohol is present in an amount of approximately between 60% and 80% by volume of the liquid treatment solution.

5. The method of claim 3 wherein the treatment solution further contains an anticalcification agent.

6. The method of claim 5 wherein the anticalcification agent is a multivalent metallic cation selected from the group consisting of a salt of $Al^{+3}$ and $Fe^{+3}$ which is soluble in the treatment solution.

7. The method of claim 6 wherein the anticalcification agent is $AlCl_3$ in a concentration range of from about 0.1M to 0.001M.

8. The method of claim 1 wherein the water-soluble aliphatic alcohol is selected from the group consisting of methanol, ethanol, propanol, and isopropanol.

9. The method of claim 8 wherein the water-soluble aliphatic alcohol is ethanol.

10. The method of claim 1 wherein the biomaterial has been cross-linked.

11. The method of claim 10 wherein the biomaterial has been crosslinked with glutaraldehyde.

12. The method of claim 1 wherein the time sufficient to render the biomaterial resistant to calcification is at least about 20 minutes.

13. The method of claim 12 wherein the time sufficient to render the biomaterial resistant to calcification is between about 24 to 96 hours.

14. The method of claim 1 wherein there is provided the further step of storing the treated biomaterial in a sterile, glutaraldehyde-free environment.

15. The method of claim 1 wherein there is provided the further step of storing the treated biomaterial in a storage solution of a lower aliphatic alcohol and glutaraldehyde.

16. The method of claim 15 wherein the storage solution is an aqueous solution containing approximately between 60% to 80% by volume of ethanol and approximately between 0.2% to 0.5% glutaraldehyde.

17. The method of claim 3 wherein the biomaterial is an aortic valve cusp and the alcohol is ethanol.

18. The method of claim 5 wherein the biomaterial is an aortic valve wall, and the anticalcification agent is an aluminum salt in ethanol.

19. The method of claim 1 wherein there is provided the further step of sterilizing the bioprosthetic tissue.

20. The method of claim 3 wherein the treatment solution is buffered to a pH in the range of between 7.0 and 7.6.

21. The method of claim 20 wherein the liquid treatment solution is buffered to a pH of 7.4.

22. The method of claim 4 wherein the alcohol is present in an amount of approximately 80% by volume of the liquid treatment solution.

23. A method of making calcification-resistant biomaterial for use in the interior of a human or animal, the method comprising the steps of:
 a) subjecting glutaraldehyde pre-treated bioprosthetic tissue, wherein the bioprosthetic tissue is a collagenous material derived from a mammalian species selected from the group consisting of bovine pericardium, porcine aortic heart valves, saphenous bypass grafts, aortic homografts, and dura mater, to an aqueous, treatment solution of at least about 50% by volume of a water-soluble C1–C3 aliphatic alcohol for a period of time between about 20 minutes and 96 hours; and
 b) rinsing the bioprosthetic tissue.

24. The method of claim 23 wherein there is provided the further step of:
 c) storing the bioprosthetic tissue in a sterile, buffered solution of approximately between 0.2% to 0.5% glutaraldehyde and at least 60% ethanol.

25. The method of claim 23 wherein the alcohol is ethanol.

26. The method of claim 23 wherein the solution further contains an anticalcification agent which is a multivalent metallic cation selected from the group consisting of a salt of $Al^{+3}$ and $Fe^{+3}$.

27. The method of claim 26 wherein the anticalcification agent is an aluminum salt in ethanol.

28. The method of claim 23 wherein the alcohol is present in an amount of approximately between 60% and 80% by volume of the treatment solution.

29. The method of claim 28 wherein the alcohol is present in an amount of approximately 80% by volume of the liquid treatment solution.

30. A method of treating a biomaterial, the method comprising the steps of:
 (1) forming a liquid treatment solution consisting essentially of a water-soluble C1–C3 aliphatic alcohol in an amount of greater than about 40% by volume and a further organic solvent, wherein the combined amount of the alcohol and organic solvent is greater than about 50% by volume, in an aqueous buffer at pH between about 6.0 and 8.0;
 (2) exposing the biomaterial, wherein the biomaterial is a collagenous material derived from a mammalian species selected from the group consisting of bovine pericardium, porcine aortic heart valves, saphenous bypass grafts, aortic homografts, and dura mater, to the liquid treatment solution for a period of time sufficient to render the biomaterial resistant to calcification; and
 (3) rinsing the exposed biomaterial in a rinsing solution.

31. The method of claim 30 wherein the treatment solution includes about 40% alcohol and 40% organic solvent.

32. A biomaterial produced by the process of claims 1 or 23 or 30.

* * * * *